United States Patent
McIntyre (10) Patent No.: US 6,177,282 B1
(45) Date of Patent: Jan. 23, 2001

(54) ANTIGENS EMBEDDED IN THERMOPLASTIC

(76) Inventor: John A. McIntyre, 6135 Autumn La., Indianaopolis, IN (US) 46220-5006

(*) Notice: Under 35 U.S.C. 154(b), the term of this patent shall be extended for 0 days.

(21) Appl. No.: 08/909,889

(22) Filed: Aug. 12, 1997

(51) Int. Cl.⁷ .................................................. G01N 33/543
(52) U.S. Cl. ........................ 436/518; 436/532; 436/533
(58) Field of Search .................................. 436/518, 532, 436/533; 428/287; 424/27; 433/4.1

(56) References Cited

U.S. PATENT DOCUMENTS

| | | | |
|---|---|---|---|
| 3,766,013 | * 10/1973 | Forgione et al. | 195/63 |
| 3,767,790 | * 10/1973 | Guttag | 424/81 |
| 4,031,201 | * 6/1977 | Lostia | 424/27 |
| 4,118,349 | 10/1978 | Bonacker et al. . | |
| 4,195,127 | * 3/1980 | Hartdegen et al. | 435/174 |
| 4,360,358 | 11/1982 | Sharma . | |
| 4,390,343 | 6/1983 | Walter . | |
| 4,407,957 | * 10/1983 | Lim | 435/178 |
| 4,459,362 | 7/1984 | Yabusaki . | |
| 4,609,707 | * 9/1986 | Nowinski et al. | 525/54.1 |
| 4,673,438 | * 6/1987 | Wittwer et al. | 106/145.1 |
| 4,727,023 | * 2/1988 | Wang et al. | 435/7.23 |
| 4,738,724 | * 4/1988 | Wittwer et al. | 106/206.1 |
| 4,752,638 | * 6/1988 | Nowinski et al. | 525/54.1 |
| 4,822,747 | * 4/1989 | Johnson et al. | 436/532 |
| 4,827,944 | 5/1989 | Nugent . | |
| 5,013,590 | * 5/1991 | Nerbe et al. | 428/36.4 |
| 5,013,669 | * 5/1991 | Peters, Jr. et al. | 436/518 |
| 5,099,857 | * 3/1992 | Baldo et al. | 128/743 |
| 5,110,833 | * 5/1992 | Mosbach | 521/50 |
| 5,234,841 | * 8/1993 | Sutton | 436/533 |
| 5,236,703 | * 8/1993 | Usala | 424/78.36 |
| 5,258,503 | * 11/1993 | Yokohari et al. | 530/415 |
| 5,277,915 | * 1/1994 | Provanchee et al. | 424/485 |
| 5,288,497 | * 2/1994 | Stanley et al. | 424/440 |
| 5,344,758 | * 9/1994 | Krilis | 433/4.1 |
| 5,372,820 | * 12/1994 | Jozefon vicz nee Dorgebray | 424/499 |
| 5,413,924 | * 5/1995 | Kosak et al. | 435/177 |
| 5,414,075 | 5/1995 | Swan et al. . | |
| 5,461,175 | * 10/1995 | Fischer et al. | 564/304 |

(List continued on next page.)

FOREIGN PATENT DOCUMENTS

| | | |
|---|---|---|
| 9010227 | * 9/1990 | (WO) . |
| WO 90/10227 | 9/1990 | (WO) . |
| WO 91/10138 | 7/1991 | (WO) . |
| 9301494 | * 1/1993 | (WO) . |

OTHER PUBLICATIONS

Lechuga, L.M. et al, Rev. Plast. Mod. vol. 70, No. 470, Aug. 1995, pp. 132–140; English Translation provided Chasin, et al, Biopharm. MFG., 1988, vol. 2, pp. 33–41.*

Kiremitci, M. et al, J. Biomater, Sci. Polymer. Edu. vol. 6(5), 1994, pp. 425–433.*

McIntyre, et al., "Phospholipid Binding Plasma Proteins...", *American Journal of Reproductive Immunology*, vol. 37, pp. 101–110 (1997).

McIntyre, et al., "The Evolution, Evaluation and Interpretation of ....", *Clinical Immunology Newsletter*, vol. 15, Issue No: 2/3, pp. 28–38 (1995).

* cited by examiner

Primary Examiner—James C. Housel
Assistant Examiner—Ginny Allen Portner
(74) Attorney, Agent, or Firm—Antonelli, Terry, Stout & Kraus, LLP (57) ABSTRACT

The invention relates to an immunoassays, binding assays, solid phase substrates (12) and other devices with an antigen or antibody or ligand or receptor (11) embedded into a solid phase substrate (12). The antigen or antibody is mixed with a molten thermoplastic and formed into the solid phase substrate (12).

6 Claims, 6 Drawing Sheets

U.S. PATENT DOCUMENTS

| | | | |
|---|---|---|---|
| 5,472,852 | * 12/1995 | Smirnov et al. | 435/13 |
| 5,506,110 | * 4/1996 | Matsuura et al. | 435/7.94 |
| 5,550,044 | * 8/1996 | Kosak et al. | 435/177 |
| 5,580,770 | * 12/1996 | Defilpysi | 435/180 |
| 5,582,907 | * 12/1996 | Pall | 428/287 |
| 5,599,552 | * 2/1997 | Dunn et al. | 424/423 |
| 5,599,660 | * 2/1997 | Ramanujam et al. | 435/4 |
| 5,695,942 | * 12/1997 | Farmilo et al. | 435/7.1 |
| 5,723,588 | * 3/1998 | Donofrio et al. | 530/815 |
| 5,739,244 | * 4/1998 | Fisk | 524/47 |
| 5,785,989 | * 7/1998 | Stanley et al. | 424/440 |
| 5,808,012 | * 9/1998 | Donofrio et al. | 525/54.1 |
| 5,821,311 | * 10/1998 | Moshbach | 526/201 |
| 5,872,198 | * 2/1999 | Moshbach | 526/221 |

ANTIGENS EMBEDDED IN THERMOPLASTIC

FIELD OF THE INVENTION

The present invention relates to the preparation of an immobilized antigen and its use in immunoassays as well and other biomedical applications.

BACKGROUND TO THE INVENTION

Immunoassays have been used for decades as a means to assay for the qualitative and quantitative presence of antigens or antibodies in a sample. Among the most common immunoassay techniques include a solid phase matrix to which either an antigen or antibody is bound. While numerous methods for attaching the antigen or antibody to the solid phase are known and several widely used, the attachment technique remains an important step in the preparation of an immunoassay. Indeed, the immobilization of an antibody or antigen to the solid phase is usually one of the first steps in preparing an immunoassay.

Swan, et al. (BSI Corporation), U.S. Pat. No. 5,414,075, disclose chemically coupling a target molecule, such as phospholipids, to a plastic support, such as polystyrene, using a multi-functional chemical coupling agent.

Sharma, U.S. Pat. No. 4,360,358, discloses the formation of an immunologically active solid phase by incorporating a low molecular reagent, such as a hapten, into a material which forms a solid polymer. This polymer is itself coated on a solid phase. The base solid phase may be polystyrene. The material forming a solid polymer includes a number of gels and the like.

Sterhan et al. (Biostar Medical Product, Inc.), World Patent 90/10227, disclose the absorption of cardiolipin, phospholipids and other materials on a solid support, such as a plastic well plate, which was previously coated with methylated bovine serum albumin.

Shah et al. (Baxter Diagnostics Inc.), World Patent 91/10138, disclose either the passive absorption or the chemical coupling of cardiolipin, phosphatidylcholine and/or cholesterol to polystyrene plates for the purposes of an ELISA (enzyme-linked immunosorbent assay). Note that all of the coating and coupling occurs after the plastic plate has been formed.

Matsuura, et al. (Yamasa Shoyu Kabushiki Kaisha), U.S. Pat. No. 5,506,110, disclose binding various phospholipids on a polystyrene well plate for the purposes of an ELISA. The antigens are passively absorbed on the solid phase. Note the assay's ability to distinguish between various antiphospholipid antibodies.

Lostia, et al. (Snam Progetti S.p.A.), U.S. Pat. No. 4,031,201, disclose the preparation of fibers incorporating antibodies or antigens. These fibers are used for a number of purposes including as a solid phase in various immunoassays. The active substance, which may be a hapten, is mixed with a polymer and the mixture is then spun through a coagulation bath to produce the solid phase in the form of fibers. Note that the polymer may be polystyrene. The fibers are porous and contain microcavities.

Peters, Jr. et al. (SmithKline Diagnostics, Inc.), U.S. Pat. No. 5,013,669, disclose an immunoassay wherein the antigen or hapten is chemically coupled to a polymer which forms a solid material. This material is coated on another solid support. The polymer is reversibly water-soluble and is chemically bound to the antigen/hapten.

Sutton, (Eastman Kodak Company), U.S. Pat. No. 5,234,841, discloses the coating of a solid phase, such as polystyrene with an antigen/hapten for use in an immunoassay. The biologically active material is dissolved in a solvent and then coated on the solid phase.

Bonacker, et al. (Behringwerke Aktiengesellschaft), U.S. Pat. No. 4,118,349, disclose immunoassays wherein the solid phase immobilized antibody or antigen is chemically bound to a polystyrene solid phase. The antibody or antigen is chemically coupled to the polystyrene carrier through a chemical coupling compound.

Yabusaki (Hana Biologies, Inc.), U.S. Pat. No. 4,459,362, discloses an immunoassay for antibodies to various phospholipids using phospholipids in suspension.

Hartdegen, et al. (W. R. Grace & Co.), U.S. Pat. No. 4,195,127, disclose immobilizing proteins, which include antibodies or antigens, in a polyurethane foam product. The antibody or antigen is mixed with a monomer or prepolymer and reacted thereto. The chemical conjugate of antigen and prepolymer is then polymerized to form the polyurethane foam. This solid phase can then be used for a number of uses. The antibody or antigen is chemically coupled to the polymer molecule.

Nowinski, et al. (Genetic Systems Corporation), U.S. Pat. Nos. 4,609,707 and 4,752,638, disclose the formation of a polymer-antibody or polymer-antigen solid material by chemically reacting the antibody or antigen to a monomer directly or indirectly to form a monomer/antibody or antigen conjugate, followed by polymerizing of the monomer. The material may then be used as a solid phase in immunoassays. The solid phase may take any form.

Johnson, et al. (Miles Inc.), U.S. Pat. No. 4,822,747, disclose immobilizing a hapten reagent on a solid phase and using it in an immunoassay. The reference teaches that the hapten is to be chemically coupled to reactive moieties on the outer surface of the polymer. Interesting, Johnson, et al. emphasizes the need to chemically bind the hapten to the solid phase as non-specifically bound haptens may be washed or slowly leached away from the solid phase.

Walter, (Miles Laboratories, Inc.), U.S. Pat. No. 4,390,343, discloses dipstick-type analytical elements where the antibody or antigen/hapten are incorporated into a gel, such as agarose, gelatin or PVP.

Immunoassays for detecting syphilis have been in widespread use for decades. Every unit of blood and patients suspected of having any sexually transmitted disease are routinely screened for syphilis by immunoassay. The techniques for screening blood for antibodies to syphilis have included VDRL (Venereal Disease Research Laboratory), RPR (rapid plasma regain), complement fixation, treponemal immobilization/adherence, FTA (fluorescent treponemal antibody) ELISA and possibly a number of other immunoassay formats also. The earliest immunoassay for phospholipids (PL) is the Wassermann reaction (ca. 1905) which is a complement fixation assay.

All immunoassay methods are dependant on antibody binding to the antigen. The antigen for syphilis serology has historically been an alcohol extract from beef heart mixed with cholesterol. The antigen (cardiolipin) was typically adsorbed onto carbon particles as a solid phase. While the antigen is not perfect, it has demonstrated its effectiveness at protecting the blood supply.

A number of other diseases also have been associated with or identified by detecting antibodies to the same PL antigens or to phospholipid binding proteins. Examples include patients with systemic lupus erythematosus (SLE) and a subset of patients identified as having anti-phospholipid syndrome. Clinical findings include recurrent venous thrombosis, recurrent arterial thrombosis, recurrent spontaneous abortion, thrombocytopenia, chorea, epilepsy, livedo and idiopathic pulmonary hypertension. Other rheumatological and collagenous diseases also present as characteristic antibodies to PL in the patient's serum. In the field of human organ transplantation, primary non-function of the organ also may appear associated with the presence of anti-phospholipid antibody (aPA). Wagenknecht et al, *Human Immunology*, 49, p. 27 (1996). Accordingly, there is a great need and numerous applications for a standardized immunoassay for aPA.

ELISAs has been in use for about 25 years to detect small amounts of antigenic substances. Today, many ELISA systems use plastic (polystyrene) 96-well plates (Microtiter plates) which have been adapted and/or modified to provide optimal binding of the antigenic substance to which antibodies have been produced. Beginning in the 1980's, the ELISA was selected for use for the detection of antibodies to antigens composed of PL and/or PL-binding plasma proteins.

The term "anti-phospholipid antibody" (aPA) refers to the conventional usage of that term in which many antibodies to PL are actually antibodies to plasma proteins which bind to phospholipids. Nonetheless, PL are considered an antigen. While not wishing to be bound by any theory, it is believed that phospholipid binding proteins do not bind aPA in the absence of another component such as PL unless the plastic containers are specifically treated such as irradiated plastic surfaces which increase the binding of certain phospholipid binding proteins. See McIntyre et al, *American Journal of Reproductive Immunology*, 37: p. 101–110 (1997). While the term "anti-phospholipid antibody" may be confusing, it is well understood in the art.

Since its inception, immunoassays used for detection of anti-phospholipid antibody (aPA) in patient blood have been fraught with problems relating to reproducibility, sensitivity and quantification. Interlaboratory comparisons of quantification of aPA are particularly in disagreement. See Wagenknecht et al, *Clinical Immunology Newsletter*, 15(2/3):28–38 (1995) for a review article on the subject. A major problem with all ELISA systems and especially with the aPA ELISA involves the important first two steps in the assay; 1. "coating" the antigenic material to the plastic surface of the microtiter plate wells and 2. "blocking" with a proteinaceous substance, often bovine serum albumin. The blocking step may remove PL from the plate because serum albumin and other proteins can bind to PL and thus they compete with the PL coated plastic plate for PL binding. Additionally, it is difficult to control the blocking step to prevent this loss.

In the aPA ELISA, PL such as cardiolipin, phosphatidylserine, phosphatidylethanolamine, phosphatidylglycerol, phosphatidyldiglycerol, phosphatidylinositol, phosphatidylcholine and phosphatidic acid are used to coat the wells of the plates. This coating step often is done in the presence of organic solvents, such as chloroform, which are desirable for their ability to keep lipids in solution. Organic solvents are undesirable, however, because they can etch plastic and thus cause unwanted light refraction when the plate contents are measured for changes in optical density, i.e., color. Also, it has been reported that up to 64% of the phospholipid antigen was removed from the plastic surface during the course of the assay. See Smolarsky, *Journal of Immunological Methods*, 38: p. 85–93 (1980) Organic solvents are not acceptable for certain proteinaceous substances which may be denatured and inactivate their binding properties.

After the PL is applied to the wells, a second problem may be oxidation of the PL containing fatty acids. The oxidation of unsaturated fatty acids causes them to become rancid and/or to cross link. Crosslinking by oxidation is the basic principle occurring in the "drying" of paints and varnishes. Oxidation has been shown to alter the antigenic properties of some PL. To avoid this problem, aPA ELISA plates often are dried under nitrogen or stored in sealed containers.

A third problem is the loss of the coated antigen due to the blocking agent and numerous wash steps required during the course of the ELISA. Historically, multiple steps in aPA ELISA plate preparation generate other problems and expenses such as the cost of labor intensive setup procedures. Due to the lack of a consensus about PL coating of the plate among laboratories who perform these assays, poor intra- and interlaboratory reproducibility has been a consistent problem.

Similar problems exist with the immobilization of other antigens and antibodies to plastic surfaces. Other binding assays and other surfaces have similar problems. Regardless of the antigen (or antibody), protein, phospholipid, carbohydrate (such as blood group antigens), or nucleic acid, all have certain inherent problems when immobilizing on a plastic surface, not the least of which is retaining their binding properties.

Many untreated plastics are hydrophobic. If a binding agent being immobilized has a hydrophobic portion, this portion will tend to adhere to the plastic surface if an aqueous carrier solute is used. Depending on the solute and surfaces being used, the complementary portion of the binding agent will tend to adhere to the plastic surface. In immunoassays, the antibody-antigen binding occurs on only a specific portion of each molecule. The same is true for other receptor/ligand binding assays. If this portion is obscured by the plastic surface, binding will be inhibited. This can lead to irreproducible results, lower than true concentrations and even false negatives.

Similar problems exist with the immobilization of any ligand or receptor in a binding assay, affinity binding or chromatography system, enzyme immobilization and for the coating of medical implants to make them more acceptable to the recipient.

The presence of or levels of antibody, antigen, or ligand in a biological sample is indicative of various conditions and is diagnostically important. For example, antibody to PL in the serum may be indicative of whether an infection remains or an autoimmune disease state is likely. Past exposure to the antigen, such as with a treated syphilis infection, without active current infection may also be detected but the antibody titer will eventually be lower as time passes, particularly IgM and IgA titers. Likewise, high levels of aPA correlate with further occurrence of thrombosis in patients with SLE. To quantify the level of antibody in blood, one must have a reproducible standard assay since there is a correlation between the number of antigen molecules on the solid support and the number of bound antibody molecules resulting from sample application.

SUMMARY OF THE INVENTION

The present invention provides a standard and stable preparation of binding partners which is easily reproduced on a large scale without relying on careful use by the operator of a solid phase binding assay.

The present invention prepares a uniform immobilized binding agent capable of binding to and insolubilizing a binding partner in a sample liquid.

The present invention distributes binding agent evenly throughout a solid material so that the distribution of binding agents on the surface is of a predefined quantity.

The present invention prepares an immobilized binding agent which will not leach or elute from a solid phase.

The present invention prepares an immobilized binding agent where a bound binding partner may be stripped off and the solid phase reused for the same or other purposes.

The present invention prepares an immobilized binding agent for affinity chromatography to separate a desired predefined binding partner from a sample.

The present invention prepares and uses an immunoassay involving the binding of a binding partner to the immobilized binding agent.

The present invention prepares and uses reusable immobilized antigens or enzymes which are embedded in the solid phase.

The present invention prepares an implant or other medical device contacting a host or host fluids, containing embedded binding agents which make the medical product, such as a vascular prosthesis, more biologically compatible to the recipient host.

The invention mixes one of the two binding substances with a fluid plastic material which is then hardened into a solid phase. The binding agent is embedded in the solid phase and the binding partner is initially free in a fluid. The solid phase with a binding agent embedded throughout it is then usable in any conventional immunoassay format where a binding agent is embedded in a solid phase.

While prior art methods for coating the plastic surfaces with PL antigens have been less than fully satisfactory, the present invention avoids the coating step which resulted in variations in coating, stability on the surface and inconsistent results. Antigen loss as noted above is eliminated as the antigen is embedded into the solid phase matrix. The present invention mixes the antigen with a thermoplastic material heated to a molten state. The mixture is then used in conventional injection and blow molding to form the solid phase. The process provides for an even distribution and constant concentration of the PL antigen in the plastic material.

The figures are drawn to illustrate certain features of the invention and are not drawn to scale with respect to other components. Furthermore, certain components are drawn schematically when numerous different designs and assay formats are possible while practicing the invention.

DESCRIPTION OF THE PREFERRED EMBODIMENT

One embodiment of the present invention relates to the incorporation of binding agents into solid phase substrates, particularly plastic materials, the products produced thereby (such as tubes, beads and multi-well plates), and binding assays using these products. While some specified examples involve an ELISA, the present invention is not limited to any particular immunoassay format provided that at least one of the ligand, receptor, antibody, antigen or hapten is embedded in a solid phase during the immunoassay. Indeed, the present invention may be used for other binding assays, some of which are exemplified below.

Figure 1:
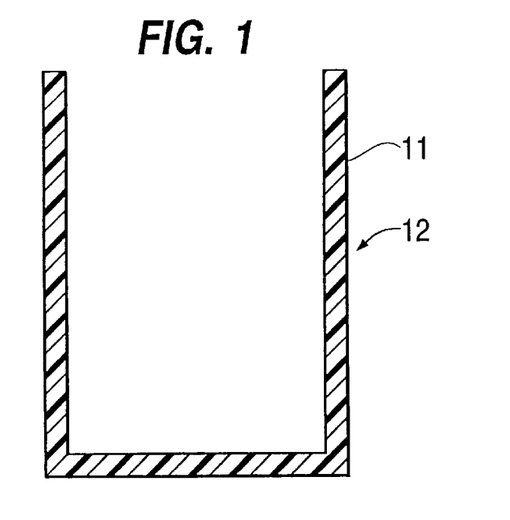
FIG. 1 is a sectional view of a test tube with a binding agent dispersed throughout it.
Figure 2:
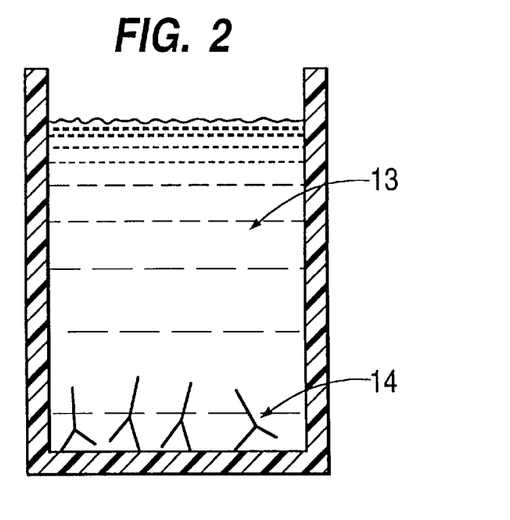
FIG. 2 is the same test tube after a sample liquid containing a binding partner is added and allowed sufficient time for the binding partner to bind to the binding agent.
Figure 3:
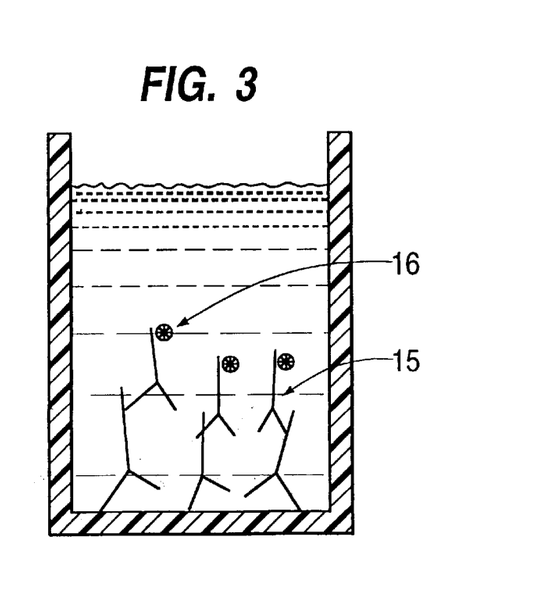
FIG. 3 is the same test tube as FIG. 2 after washing and adding a labeling agent (labeled antibody or protein G) which binds to the binding partner insolubilized on the test tube.
Figure 4:
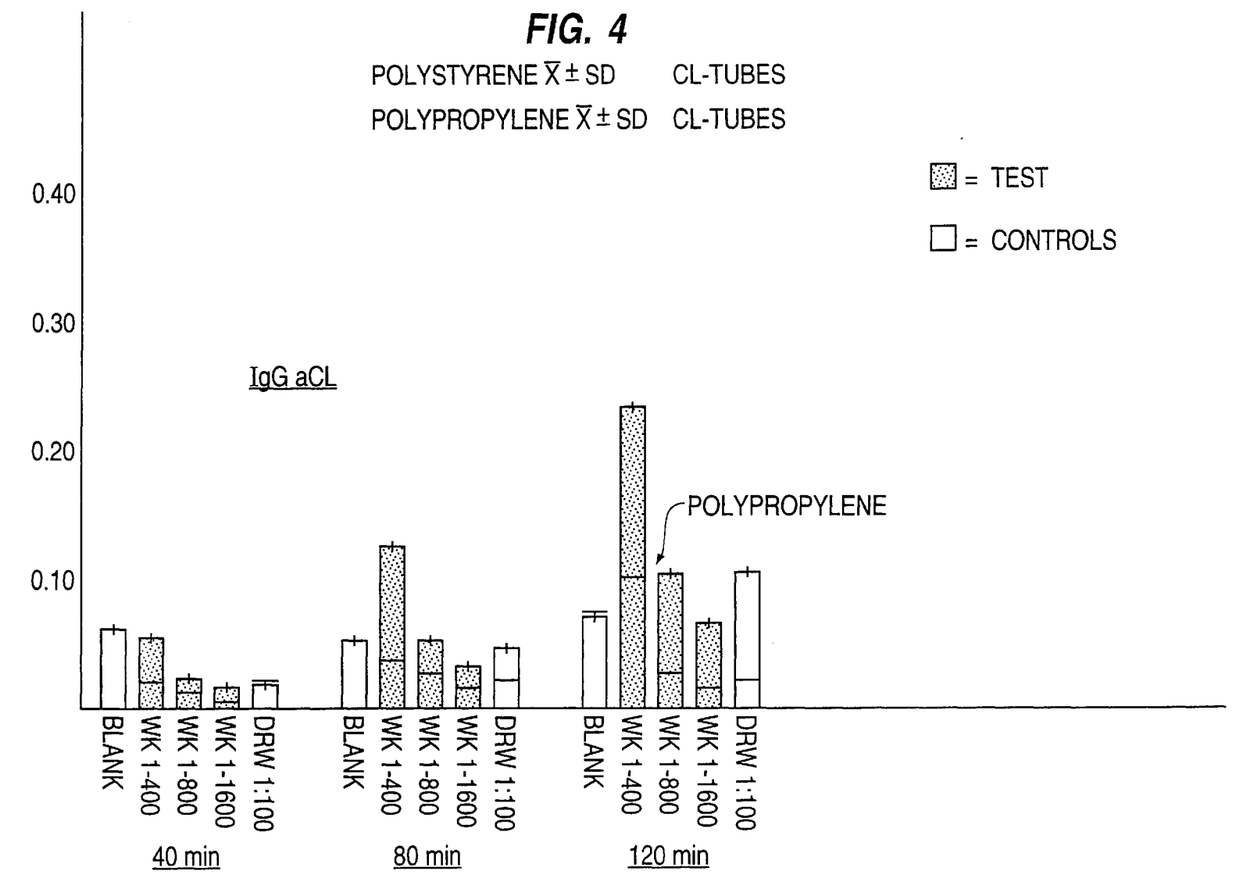
FIGS. 4–8 are graphs showing data for detecting aPA using tubes which contain PL embedded therein.
Figure 5:
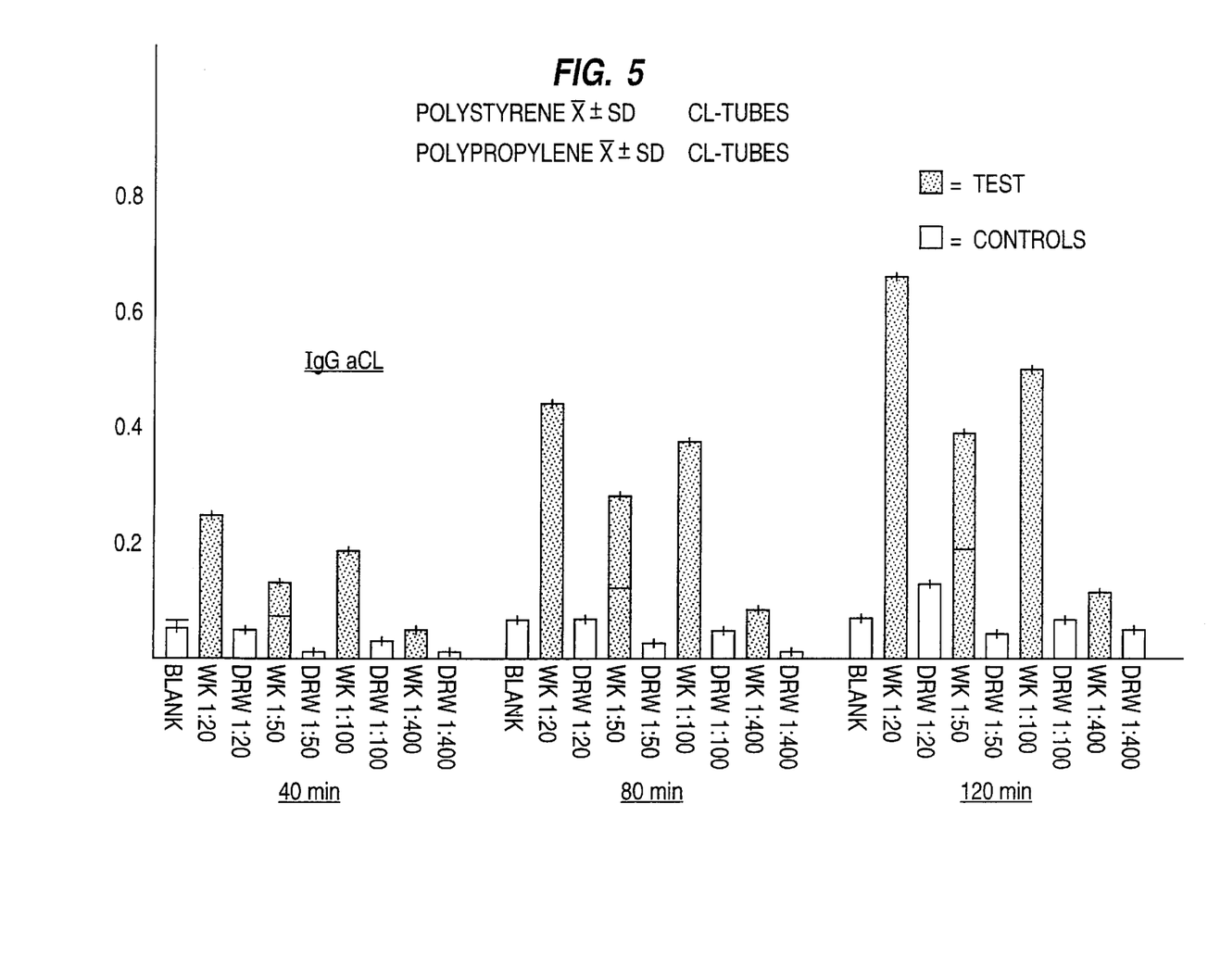
Figure 6:
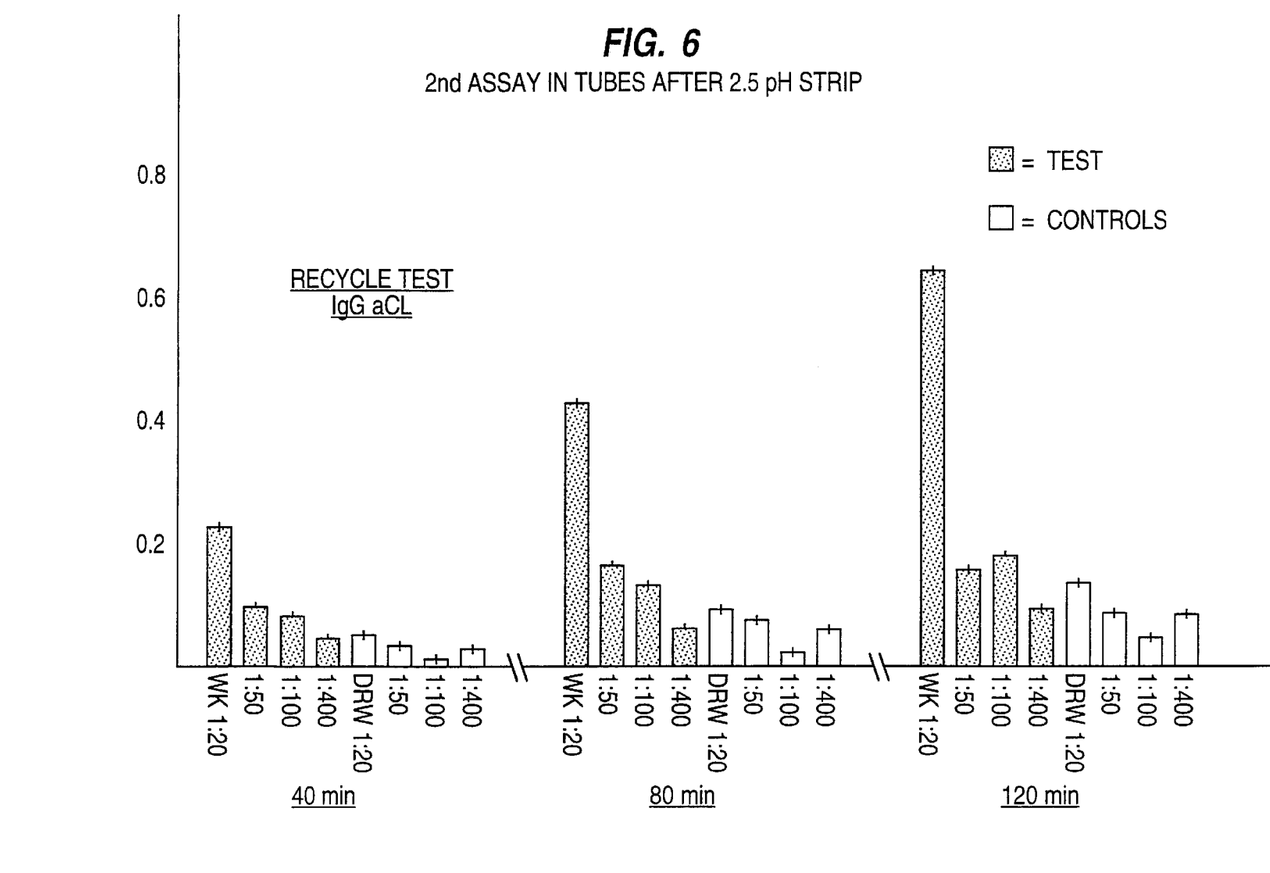
Figure 7:
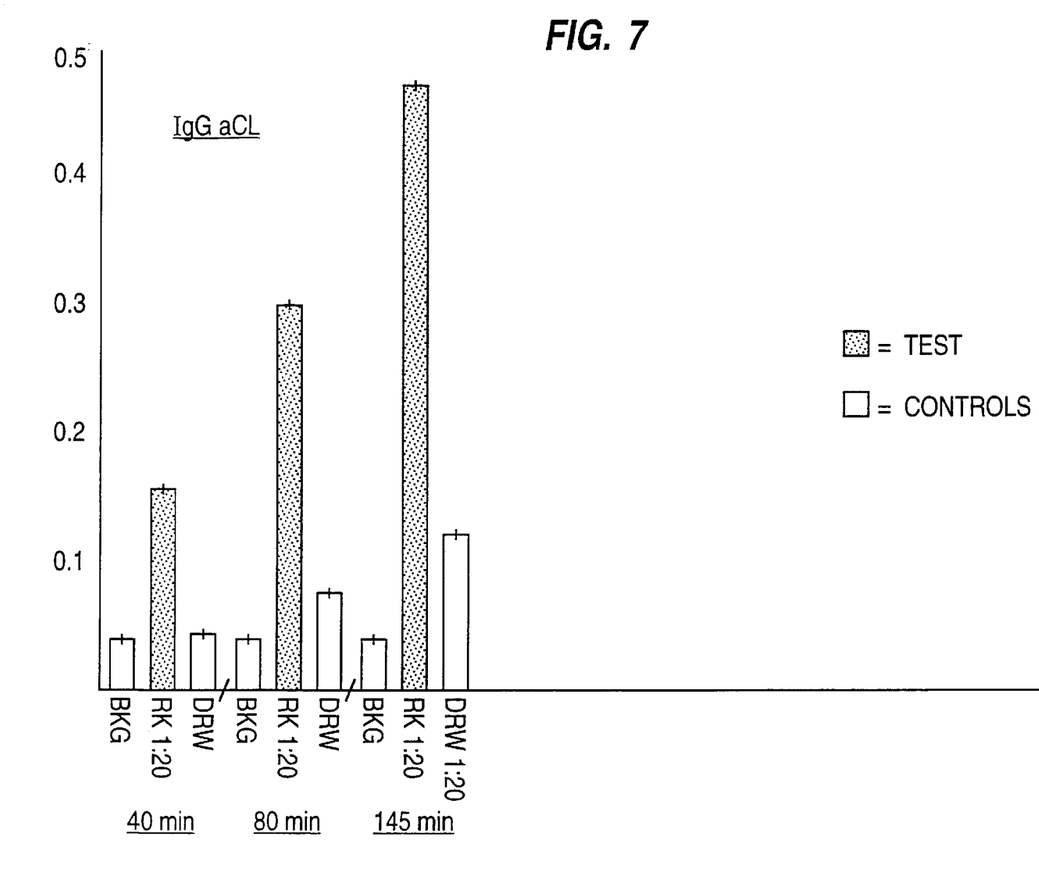

The binding agent is incorporated into a plastic material to prepare a solid phase embedded binding agent for use in an assay. In the solid phase substrate 12, the binding agent 11 is uniformly distributed throughout and embedded in the solid phase substrate 12. The solid phase substrate 12 may be in the form of a container. A liquid sample 13 containing a binding partner 14 is added to the container and the binding partner binds to the binding agent. As depicted in FIG. 2, the binding partner may be an antibody molecule which has been enlarged for easy visualization. The liquid sample is then decanted or aspirated and washed. A labeling agent 15 is then added to the container which binds to the binding partner 14. The container is again decanted or aspirated and washed to remove any unbound labeling agent. The label 16 is then detected in a manner appropriate for the particular label. When using a fluorescent label, the presence of the label may be directly observed by exposing it to appropriate wavelengths of light and observing the emission of other wavelengths corresponding to the fluorescent label. The label may be detected qualitatively or measured quantitatively and either bound to the solid phase substrate or in the removed liquid containing the unbound labeling agent.

While the solid phase substrate 12 in the form of a container is depicted as being plastic, it should be recognized that other materials may be used. Likewise, the binding agent 11 is shown as stippling merely to depict its through distribution throughout the solid phase substrate. In reality, the binding agent may be a molecule which is relatively much smaller than the dots shown. Likewise, the antibody molecules used for the binding partner and labeling agent are actually molecules and are shown vastly larger than fact. Still further, the labeling agent may be either larger (in the example of a bead) or smaller (in the example of a radioactive atom) than the asterisk shown.

The terms antibody, antigen, hapten, ligand and receptor are used interchangeably throughout this specification depending on the particular application being illustrated. All of these are considered binding substances. The terms "binding agent" and "binding partner" are used to encompass any of these components. For ease of description, the term "binding agent" refers to the component which is embedded in the solid phase and the term "binding partner" refers to the component which is free in a liquid and binds to the previously embedded binding agent to become insolubilized.

The entire object need not be made of the solid phase composition of the present invention, rather only the solid phase portion in contact with the liquid sample needs to be made of such a material. For example, wells or a strip of wells of a multi-well plate may be made of the composition of the present invention whereas the balance of the multi-well plate may be made of any conventional plastic or even metal. This arrangement permits one to remove an individual well for further analysis. Also, since the composition of the present invention is more expensive than the solid phase material without the binding agent, beneficial economies result from using the combination to make certain parts which are contacted with the liquid containing the sample.

The physical steps involved include mixing the binding agent with a material which is to become the solid phase or substrate. When the material is a thermoplastic, the binding agent to be embedded is mixed with a small plastic pellet stock and heated until molten or the binding agent may be mixed with the molten plastic itself. Uniformity in mixing the binding agent and the plastic pellets was enhanced due to static electricity generated during mixing which caused a more even coating on the plastic pellets and a through distribution throughout the mixture. The molten plastic is then formed into a plastic substrate of any desired shape. The binding agent is distributed throughout the plastic substrate. No chemical reaction need occur between the plastic substrate and the binding agent, nor is a chemical reaction particularly desirable. Examples of suitable thermoplastic polymers include polystyrene, polyethylene, polypropylene, polycarbonate, polyethylene terephalate, polyester (e.g. Dacron), polyurethane, polyolefin, polyvinyl alcohol, PVP and other polymers used in contact with tissues or biological fluids.

Other plastic materials such as thermosetting polymers may be used. In such a situation, the binding agent is mixed with the monomers or oligomers which are then heated to polymerize or cross-link the composition, thereby entrapping the binding agent. The plastic substrate may also be made by chemical, ultraviolet light or other non-thermal polymerization methods as well. A variety of hardeners, clarifiers, and plasticizers may be added to give the substrate its desired physical properties. In such a situation, the binding agent may be mixed with a substrate forming material (e.g. monomers) prior to or simultaneous with the addition of the hardening agent or the polymerization agent. Examples include epoxies and some of the same polymers listed above under thermoplastic polymers.

While the term "plastic" usually refers to organic polymers having certain physical properties in the present invention. In the present invention, any material which was fluid prior to mixing the binding agent and forms a solid material afterwards is acceptable. Thus, the term "plastic-substrate" need not even be made of what is conventionally called plastic but may include foams, rubbers, gels, etc. provided that the solid material is formed into an acceptable solid phase for a binding assay. Other examples include, calcium alginate, potassium carrageen, gelatin/collagen which is hardened, natural gums, etc. Non-polymers may also be used such as waxes, alloys, ceramics, low melting point glass, emulsions, particularly when later dried to remove water or other solvent. Also, a solid material may be mixed with an antigen and a solvent and then the solvent evaporated to leave antigen embedded in solid material. A suitable solvent as well as a good oil phase in an emulsion is a volatile silicone (i.e. cyclomethicone). Even impractical examples, such as water cooled to form ice provided that temperatures below freezing are maintained, may be used.

The binding agent containing solid phase has a distinct advantage over other insolubilized components in conventional binding assays. In the present invention, when the assay is complete, one may strip bound binding partner using dilute acid, denaturing or other rather harsh techniques which could not be used if the binding agent were merely adsorbed to the solid phase. This permits one to reuse the same solid phase which saves time and effort calibrating a new solid phase. The unique nature of embedding the binding agent in a solid phase in accordance with the present invention permits one to expose the binding agent to otherwise unacceptable chemical and/or physical conditions.

Depending on the properties of the binding agent, the plastic and the mold or other forming means, the binding agent may naturally be concentrated at the surface of the plastic substrate formed. Also, when the binding agent has different portions with different properties, the binding agent may preferentially be held in a particular configuration. For example, in a hydrophobic plastic, such as polystyrene, a binding substrate having both a hydrophilic and a hydrophobic moiety, such as proteinaceous cell membrane bound receptor, the hydrophilic portion is more likely to be exposed to the surface of the plastic substrate. This orientation may be enhanced by using a more hydrophilic mold or hydrophilic cooling fluid contacting the plastic substrate.

The binding agent may consist of an additional component other than a binding moiety. In another embodiment of the present invention, the binding agent may first be chemically coupled to another chemical which is readily associated with the material forming the solid phase substrate. For example, when using a hydrophobic substrate and a very hydrophilic prospective binding agent, it may be advantageous to first chemically react a hydrophobic moiety to the prospective binding agent so that a portion of the total binding agent readily mixes with the hydrophobic substrate. Alternatively, one may add a surfactant or other composition to the material to become the solid phase to aid in the adherence, distribution and embedding of the binding agent in the solid phase substrate. Also, one may embed only a hydrophobic compound which reacts with and binds to the binding agent later. For example, one may mix protein G with a molten material which is molded into a tube and cooled. An antibody is added to the tube and allowed to bind to protein G, the fluid is then decanted and the tube washed. The antibody-protein G complex is then the binding agent for an immunoassay or for affinity purification for an antigen.

The amount of binding agent present in the solid phase may vary widely; for example, from about 0.00000001 to about 500 weight parts per 1000 weight parts of material forming the solid phase.

While all binding agents have certain temperature and chemical limitations, the material forming the plastic substrate may be carefully chosen or modified to accommodate these temperature and chemical limitations. Proteins, such as antibodies and antigens, are well known to denature and loose their biological properties at abnormal temperatures. However, the same proteins may retain their biological properties once exposed to denaturing temperatures in the present invention due to embedding in the solid phase substrate. Other binding agents such as PL and DNA are less sensitive to heat. Thus, depending on the binding agent employed, one must judiciously choose a material to become a solid substrate and the conditions needed to solidify it.

For example, certain polystyrenes become molten at a relatively low temperature. These temperatures are compatible with binding agents made of polynucleotides, many proteins, lipids and most organic compounds. Indeed, certain polystyrenes become molten at temperatures only twice as hot as those used in the preparation of antigens prior to running them in a polyacrylamide gel, particularly the heat denaturing step. The temperature at which thermoplastic polystyrene becomes molten may be further lowered by the addition of various chemicals. The modification of the physical and optical properties of plastic materials is known per se. The weight amount of binding agent being added is trivially small compared to the weight amount of plastic and therefore is unlikely to significantly affect its properties. The same can be said for using other substrate materials.

Any of the conventional binding assay formats may be used provided that the binding agent is first embedded in a solid phase before adding a binding partner. The patent literature is replete with dozens of different binding formats in the immunoassay, nucleic acid hybridization assay and biospecific binding assay arts. Common binding formats include sandwich assays which are shown in FIGS. 2–3. Competitive binding assays may be used where a second binding partner, is added before, during or after adding the binding partner so that they compete for binding to the binding agent. Alternatively, a labeling agent may be used to bind to the binding partner in competition with the binding agent. Usually either the binding partner or the second binding partner are labeled directly or indirectly by a labeling agent for easy detection of bound or free label.

A sample refers to a binding partner containing composition which may be from any source. The binding partner, and perhaps other components, in the sample is solubilized in a fluid before use in a binding assay according to the present invention. The sample is preferably a biological sample, more preferably a biological fluid.

One of the binding substances may be directly measured by enzymatic activity or the like based solely on its presence or its activity being enhanced or inhibited by the binding agent binding to the binding partner. For example, if the binding agent is an enzyme and the binding partner is an inhibitor (or vice versa), one may directly measure the presence of the binding partner in an added sample. Likewise if one of the binding substances is an enzyme in need of a substrate, energy source, cofactor, coenzyme or vitamin for activity, the presence of any of these as a binding substance in a sample may be detected by measuring for enzyme activity. The reverse assay for the presence of the enzyme may also be used.

The binding agent and binding partner may have a wide variety of chemical structures, provided that they bind to each other in a manner that is not easily unbound by simple washing. The binding is preferably a specific binding but it may be of a more general nature. Electrostatic (e.g. van der Waals forces), chemical (covalent bonding) and physical (dimensionally a good fit) forces may be involved or constitute the binding properties.

The binding affinity and avidity may vary depending on the needs required for each application. For example, for some assays, a highly specific binding may be essential. For other techniques, a more generic binding property may be all that is needed. Thus, a plural number of embedded substances may be desirable.

These bindable components may be proteins (which includes lipoproteins, glycoproteins, metalloproteins, fragments and subunits), more preferably antibodies or fragments thereof (Fab, Fc, Fab2, etc.), antigens, enzymes, hormones, cell receptors, microorganisms or viral particles. Other chemical structures such as lipids, polysaccharides (especially bacterial antigens, major and minora blood group antigens), vitamins, enzyme substrates, coenzymes, co-factors, bound metal ions, polynucleotides, and other organic compounds (such as a metabolite, cyclodextrin, monosaccharide or chelating agent) may be used as one or both of the binding agent and binding partner. The binding agent and/or binding partner may be a fraction of a molecule provided that it retains the binding properties.

For many binding assay formats, a labeling agent is needed in addition to the binding agent and binding partner to determine whether the two binding substances actually bind to each other. The labeling agent is a composition, usually a conjugated chemical compound which has two properties. First, the labeling agent must contain a label; second, the labeling agent must physically or chemically bind to the binding partner or the binding agent. Typically, these two properties belong to different portions of the labeling agent wherein the two portions are chemically coupled together.

Examples of suitable labels include: a radioactive moiety, an enzyme or portion thereof, an enzyme substrate, a fluorescent moiety, a chemiluminescent moiety, a quencher, a moiety which reflects or adsorbs light or other electromagnetic radiation, a magnetic, paramagnetic or supermagnetic particle, a chemical detectable by magnetic resonance, a solid or porous particle or sheet or any moiety which is readily detectable directly or which interacts with another substance (such as another chemical moiety, a polymerization initiator, etc.) to result in a detectable change.

Examples of the portion of the labeling agent which binds to the binding partner include: an antibody, an antigen, a hapten, protein A or G, DNA, an adsorbent of the binding partner or binding agent, biotin, avidin/strepavidin, and moieties which chemically react with the binding partner or binding agent.

The detecting agent may be in plural portions such as a rabbit anti-mouse IgG antibody labeled with the enzyme glucose oxidase and separately free in another solution, the enzyme substrate glucose, a second enzyme peroxidase and 3,3',5,5' tetramethylbenzidine as a chromogen.

In another embodiment of the present invention, the binding agent-containing solid phase may be used as the solid phase in a chromatography separation. In such a system, the solid phase is prepared in the same manner as for binding assays with the possible exception of using a different shaped solid phase. For chromatography column packings, a large number of small particles is the preferred solid phase. The binding agent constitutes the active principle interacting with the substance in the fluid to be separated or purified. Such a system is particularly advantageous for affinity chromatography but may also be used with other types of chromatography. Note that the column packing permits economical reuse for the same or other applications without recoating a solid phase column packing.

The binding agent-containing solid phase may be used as an adsorbent without chromatographic separation. In this situation, it is desirable to remove a binding partner from a liquid sample because it is toxic or otherwise undesirable. For such an adsorption, the liquid sample is contacted with the binding agent-containing solid phase under conditions permitting binding and then the solid and liquid are separated. Examples include using erythrocytes, platelets, cells or cell lines or lyophilized versions thereof as the binding agent to bind to and adsorb non-specific binding substances which may interfere with an assay. The binding agent-containing solid phase may then be regenerated by stripping off the bound binding partner using extremes of pH, ionic conditions and even harsh chemicals and/or conditions.

Another embodiment of the present invention is to immobilize enzymes to a solid phase by incorporating the enzyme per se into the solid phase in the same manner as the binding agent was incorporated. Alternatively, an enzyme binding composition may be incorporated into the solid phase. Examples of enzyme binding compositions include, antibodies to the enzyme, enzyme adsorbents, enzyme substrates, inhibitors, coenzymes, vitamins and cofactors. Examples include biotin for binding to avidin/strepavidin, ATP and NAD(P)/NAD(P)H. The enzymes may be immobilized by chemical reaction to the solid phase bound enzyme binding composition through a separate reaction. The immobilized enzyme may be used for any of the conventional immobilized enzyme uses which are known per se.

In another embodiment of the present invention, the solid phase embedded binding agent may be used for the detection of or separation of large particles. The solid phase may act as a labeling means for a binding agent. For example, to count the number of various subsets of T-lymphocytes in a blood sample, one may use one of the CD series of monoclonal antibodies as the binding agent. The solid phase may be prepared by melting small wax particles (beeswax, castor wax, fatty alcohols, silicone waxes, etc.), fluorescein, the CD monoclonal antibody and a solvent under gentle heat and mixing followed by spraying the liquid into a cooling fluid (such as air) to form small solid particles to be used as the solid phase. When these particles are mixed with the blood sample, the antibody may bind to the corresponding subset of T-lymphocytes making them easily detectable and countable by automated optical systems such as a fluorescent activated cell sorter (FACS).

In a similar mode, small solid particles containing the binding agent may be used in agglutination assays for a binding partner in a sample. However, in such an assay, it is preferable for the binding partner be capable of binding two or more binding sites or another reagent capable of binding two or more binding partners or binding agents may be added to induce apparent agglutination of the particles depending on whether the binding partner is present or not in the sample.

Still another embodiment of the present invention involves a number of polynucleotide hybridization assays and techniques for detecting or sequencing target polynucleotides in a sample. In this system, the solid phase contains a polynucleotide as the binding agent. The binding partner is the target polynucleotide as a binding partner which may bind by hybridization to the binding agent. The detection steps are known per se in the DNA hybridization assay field.

In another embodiment of the present invention, the solid phase substrate may be formed into a medical implant or other medical device which contacts host tissues or fluids. The substrate may be made more compatible with host tissues or fluids by implanting substances in the same manner as used for binding assays. The choice of substances would be the same as are conventionally used to coat medical implants and devices for the same purpose. Since an embedded substance is expected to represent a tighter bond than simple coating, medical implants and devices may be superior and perhaps more economical to manufacture.

An example of a preferred medical implant is an arterial prosthesis containing Dacron polyester as the solid phase and containing phospholipids embedded therein. Cholesterol, heparin/heparan, glucosaminoglycans, complement inactivating proteins and other components may also be embedded. Likewise, polyurethane may be substituted for Dacron, particularly with other types of medical prosthesis. Other medical devices, tubes, blood bags etc, may be likewise embedded with naturalizing substances to make the device more compatible.

The solid phase which constitutes the plastic substrate may be molded into any form such as particles, beads, tubes, multi-well plates, etc. The solid phase may be monolithic or porous depending on the potential binding partner and the amounts of binding agent and binding partner present to be bound.

BENEFITS RELATING TO THE INVENTION

The ability to successfully impregnate plastic ware with an antigen can lead to many advances in ELISA technology as well as in other biomedical applications, both diagnostic and clinical. With regard to PL antigens, the impregnation in plastic process can improve the ELISA by:

1) Providing even distribution and constant concentrations of antigen in the plate wells.
2) Eliminating loss of antigen during washing procedures.
3) Shortening the time of the test and decreasing the amount of technologist labor.
4) Providing improvements in both intra- and interlaboratory consistency and standardization.
5) Allow reuse of plastic ware for additional tests and/or procedures. Other benefits of this technology are the manufacture of antigen impregnated plastic beads for affinity purification of specific antibodies and PL-binding plasma proteins or receptors. The inclusion of PL in plastics used for medical devices, for example, artificial valves and vessel grafts would provide a more natural or biological surface, i.e. less thrombogenic, for contact by body fluids.

EXAMPLE 1

Five pounds of polystyrene beads and 500 mg of lyophilized cardiolipin were mixed by a steel rod in a stainless steel bowl. This mixing was facilitated by static electricity as the cardiolipin was thoroughly distributed throughout the polystyrene pellet stock. The mixture was extruded in a heated auger which melted the polystyrene and injected in into a mold for 50 cc conical tubes.

The molten material was solidified by cooling. The finished conical tube was then removed from the mold and was ready for immediate use without the addition of any antigenic coating.

EXAMPLE 2

The tubes produced in Example 1 were then blocked by incubating a 10% bovine serum albumin solution in the tubes for one hour at room temperature. The blocked tubes were tested to ascertain if the cardiolipin retained its antigenic and plasma protein binding properties and functioned normally under conditions suitable for an ELISA. Liquid serum samples known to contain aPA and liquid serum samples known not to contain aPA were diluted 1:20, 1:50, 1:100 and 1:400 and added to different tubes and conditions adjusted to permit antibody-antigen binding for 40, 80 and 120 minutes. The liquid was decanted from the tube and the inside of the tubes was gently washed four times to remove any unbound antibody. An enzyme (alkaline phosphatase or horseradish peroxidase) labeled goat or monoclonal mouse antibody directed to human IgG, A or M was added to the tube and allowed to bind to any human antibodies present for one hour. The labeled antibody was then decanted from the tube and the inside of the tube gently washed four times to remove any unbound labeled antibody. Assay reagents containing an appropriate substrate for each enzyme was added to the tube. After reacting with the enzymes, the substrate directly or indirectly formed a product which is spectrophotometrically detectable. For samples which did not contain aPA, only background was spectrophotometrically detectable. The data is shown graphically in FIGS. 4–7.

EXAMPLE 3

50 cc tubes of polypropylene containing cardiolipin antigen were also prepared by the same manner as in Example 1 except for substituting polypropylene for polystyrene. The polypropylene containing tubes were then used in an ELISA using the same techniques and reagents as in Example 2. While the results were inferior to those using polystyrene, the assay was successful at qualitative and quantitative detection of aPA in serum samples.

EXAMPLE 4

After performing the immunoassay of Example 2 or 3, the antibody contents of the tubes were stripped by washing in a 2.5 pH buffer. The cardiolipin impregnated tubes were then reused and the results were essentially the same. Even after use for the third time, the variation was less than 5% from the data obtained using virgin tubes. Thus the antigenic properties of the PL were not affected by the manufacturing of the plastic ware and subsequent stripping of antibodies.

EXAMPLE 5

Figure 8A:
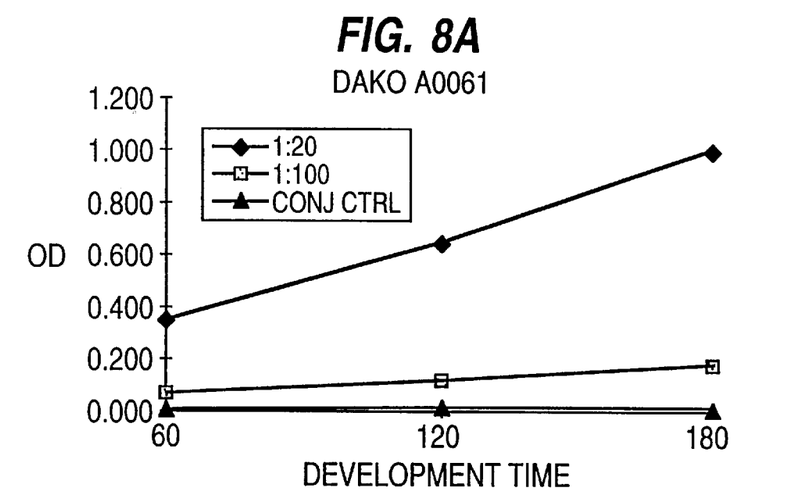
Figure 8B:
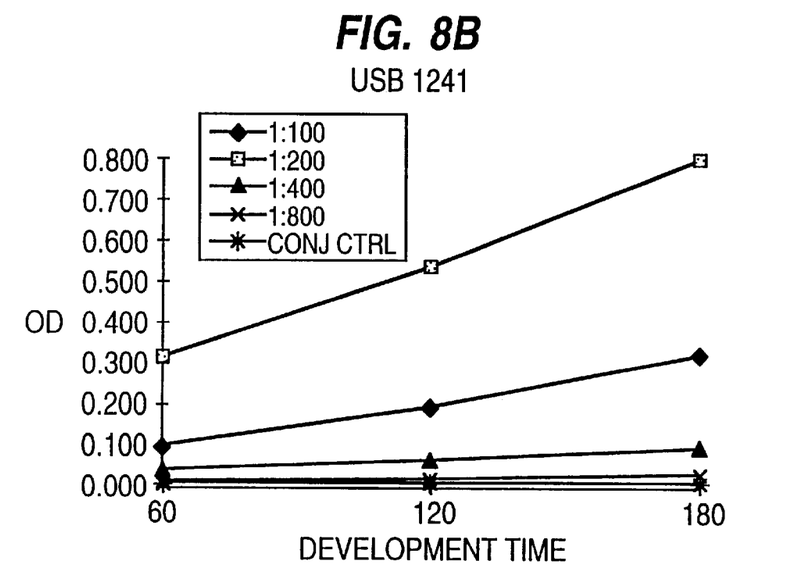

The method of Examples 1 and 2 was repeated using one gram of lyophilized transferrin and an anti-transferrin antibody in lieu of 500 µg of lyophilized cardiolipin and aPA. The assay method was similar but differed by blocking for 75 minutes, washing with 4 ml 0.05% Tween 20/TBS four times each time, using the following antibodies (0.5 ml diluted in 1% BSA) for 65 minutes for primary antibodies, 60 minutes for secondary antibodies (1:1000 dilution) and 5 ml substrate incubated at 37° C. for 60, 120 and 180 minutes followed by transferring 0.05 ml to microtiter wells containing 0.075 ml 3M NaOH. The following antibodies were used: Dako rabbit anti-human transferrin, anti-rabbit conjugate, USB goat anti-mouse transferrin 1241, and anti-goat conjugate. Comparable results were obtained demonstrating that anti-transferrin antibodies could be detected quantitatively. This data is shown in FIG. 8.

EXAMPLE 6

Five pounds of polystyrene stock pellets are mixed with 50 ng lyophilized oligonucleotide with a poly-T tail having an average length of greater than about 1.0 kb by a steel rod in a stainless steel bowl in a manner similar to Example 1 to thoroughly distribute the oligonucleotide throughout the polystyrene pellets. The mixture is extruded in a heated auger which melts the polystyrene and injects the mixture into a mold for 50 cc conical tubes.

The molten material is solidified by cooling. The finished conical tube is then removed from the mold and is ready for immediate use without the addition of any polynucleotide coating.

EXAMPLE 7

The tubes produced in Example 6 are then filled with a hybridization buffer containing 0.5 ng of sample DNA having an average length of about 600 bp and a sequence complementary to the oligonucleotide embedded in the plastic. The sample DNA has incorporated digoxigenen on approximately 10% of the TTP's in the sample DNA sequence. Control tubes omit addition of the sample DNA. The tubes are placed in a boiling water bath until the temperature of the hybridization buffer remains above 90° C. for two minutes. The tubes are removed and allowed to cool to the optimal hybridization temperature for the oligo-nucleotide and remain at that temperature for 60 minutes. The liquid is decanted from the tubes and they are washed with a series of high salt buffers. The tubes are blocked with 10% bovine serum albumin, a blocking agent, for 30 minutes at room temperature. After the blocking agent is decanted, buffer containing alkaline phosphatase labeled antibody to digoxigenen is added and incubated at room temperature for 60 minutes. The tubes are washed 3 times with a saline buffer. Paranitro-phenylphosphate in diethanolamine buffer is added and the tubes are incubated in the dark for 60 minutes. The amount of color development is determined spectrophotometrically and compared to control tubes in which no sample DNA is added to determine the presence of alkaline phosphatase indicating the tubes with incorporated DNA effectively serve as a solid phase for a DNA binding assay.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All references referred to above are incorporated by reference in its entirety.

What is claimed is:

1. A binding assay for detecting the presence of a binding partner comprising;
    contacting a sample suspected of containing the binding partner with a binding agent-containing monolithic solid material having a binding agent evenly dispersed throughout said solid material, wherein the binding agent is not chemically coupled to the solid material, said binding partner being bindable to the binding agent, wherein said sample is contacted for a sufficient time and under sufficient conditions to permit the binding partner to bind to the binding agent, and
    detecting the presence or absence of binding of the binding partner to the binding agent, wherein said binding agent is a phospholipid.

2. A binding agent-containing monolithic solid material having a binding agent evenly dispersed throughout a monolithic solid material, wherein the binding agent is not chemically coupled to the monolithic solid material, wherein the binding agent comprises a lipid or phospholipid, and wherein the binding agent-containing monolithic solid material binds to antibodies associated with a condition selected from the group consisting of systemic lupus erythematosus, venus thrombosis, recurrent arterial thrombosis, recurrent spontaneous abortion, thrombocytopenia, chorea, epilepsy, livedo, idiopathic pulmonary hypertension, rheumatological conditions and collagenous diseases.

3. A binding assay for detecting the presence of a binding partner comprising;
    contacting a sample suspected of containing the binding partner with a binding agent-containing monolithic solid material having a binding agent evenly dispersed throughout said solid material, wherein the binding agent is not chemically coupled to the solid material, said binding partner being bindable to the binding agent, wherein said sample is contacted for a sufficient time and under sufficient conditions to permit the binding partner to bind to the binding agent, and
    detecting the presence or absence of binding of the binding partner to the binding agent, wherein the assay is performed for the detection of phospholipid antigens.

4. A binding assay for detecting the presence of a binding partner comprising;
    contacting a sample suspected of containing the binding partner with a binding agent-containing monolithic solid material having a binding agent evenly dispersed throughout said solid material, wherein the binding agent is not chemically coupled to the solid material, said binding partner being bindable to the binding agent, wherein said sample is contacted for a sufficient time and under sufficient conditions to permit the binding partner to bind to the binding agent, and detecting the presence or absence of binding of the binding partner to the binding agent, wherein the assay is performed for the detection of phospholipid binding proteins.

5. A binding assay for detecting the presence of a binding partner comprising;

contacting a sample suspected of containing the binding partner with a binding agent-containing monolithic solid material having a binding agent evenly dispersed throughout said solid material, wherein the binding agent is not chemically coupled to the solid material, said binding partner being bindable to the binding agent, wherein said sample is contacted for a sufficient time and under sufficient conditions to permit the binding partner to bind to the binding agent, and detecting the presence or absence of binding of the binding partner to the binding agent, wherein the assay is performed for the detection of phospholipid antigens or phospholipid binding proteins associated with a condition selected from the group consisting of systemic lupus erythematosus, venus thrombosis, recurrent arterial thrombosis, recurrent spontaneous abortion, thrombocytopenia, chorea, epilepsy, livedo, idiopathic pulmonary hypertension, rheumatological conditions and collagenous diseases.

6. A binding agent-containing monolithic solid material having a binding agent evenly dispersed throughout a monolithic solid material, wherein the binding agent is not chemically coupled to the monolithic solid material, wherein the binding agent comprises a lipid or phospholipid, and wherein the assay is performed for the detection of phospholipid binding proteins associated with a condition selected from the group consisting of systemic lupus erythematosus, venus thrombosis, recurrent arterial thrombosis, recurrent spontaneous abortion, thrombocytopenia, chorea, epilepsy, livedo, idiopathic pulmonary hypertension, rheumatological conditions and collagenous diseases.

* * * * *